United States Patent [19]
Jensen et al.

[11] Patent Number: 5,659,977
[45] Date of Patent: Aug. 26, 1997

[54] INTEGRATED MICROALGAE PRODUCTION AND ELECTRICITY COGENERATION

[75] Inventors: Glenn Jensen, Kailua-Kona, Hi.; Eric H. Reichl, Princeton, N.J.

[73] Assignee: Cyanotech Corporation, Hi.

[21] Appl. No.: 641,159

[22] Filed: Apr. 29, 1996

[51] Int. Cl.⁶ .................................................. F26B 21/06
[52] U.S. Cl. ........................... 34/547; 34/548; 34/61; 34/62; 34/66; 34/82; 34/85; 34/86; 34/90; 435/292.1; 60/648
[58] Field of Search ........................ 34/526, 535, 547, 34/548, 586, 61, 62, 66, 82, 85, 86, 90; 110/245; 432/58; 435/292.1; 47/1.406, 1.407; 60/648

[56] References Cited

U.S. PATENT DOCUMENTS

| | | | |
|---|---|---|---|
| 2,815,607 | 12/1957 | Schroeder | 435/292.1 |
| 3,131,035 | 4/1964 | Erickson | 34/86 |
| 3,420,739 | 1/1969 | Bongers et al. | 435/292.1 |
| 3,955,317 | 5/1976 | Gudin | 435/292.1 |
| 4,084,346 | 4/1978 | Stengel et al. | 435/292.1 |
| 4,240,581 | 12/1980 | Fowler | 34/86 |
| 4,653,198 | 3/1987 | Alsaker | 34/86 |
| 4,868,123 | 9/1989 | Berson et al. | 435/292.1 |
| 4,989,344 | 2/1991 | Glorioso | 34/86 |
| 5,276,977 | 1/1994 | Cysewski | 34/371 |

*Primary Examiner*—John M. Sollecito
*Assistant Examiner*—Steve Gravini
*Attorney, Agent, or Firm*—Harry B. Keck

[57] ABSTRACT

An integrated plant including a microalgae production plant for growing, harvesting and drying algae and a fossil fuel-motor-generator plant producing electrical energy. A fossil fuel engine produces hot exhaust gas from which sensible heat dries the algae. The drying may be direct from the exhaust gas or may be indirect with the hot exhaust gas exchanging sensible heat with a recirculating stream of inert gas. Carbon dioxide from the exhaust gas is recovered for use as a nutrient in the microalgae production plant. Electrical energy from the generator is used to drive motors and/or produce artificial illumination and/or drive pumps, motors and controls in the microalgae production plant.

6 Claims, 2 Drawing Sheets

INTEGRATED MICROALGAE PRODUCTION AND ELECTRICITY COGENERATION

CROSS REFERENCE TO RELATED APPLICATIONS (IF ANY)

NONE

BACKGROUND OF THE INVENTION

1. Field of the Invention

This invention concerns an integrated installation involving a microalgae production plant for growing, drying and harvesting microalgae, and a companion co-generation motor-generator unit developing electrical energy for use throughout the integrated plant and for developing hot exhaust gases as a source of process heat containing carbon dioxide which is useful in the integrated process.

2. Description of the Prior Art

Microalgae production has developed as an industry for growing selective algae and harvesting and processing the algae as a source of food, chemicals and pharmaceuticals. A microalgae production plant includes a culture pond containing warm water having dissolved carbon dioxide, and containing means for collecting and drying microalgae which grow in the culture pond. Microalgae production is frequently carried out in remote regions such as tropical islands, which are warm and have abundant sunshine. In these remote regions most basic requirements must be imported at significant cost: e.g., fuel, electrical power, carbon dioxide.

A microalgae production plant is described in U.S. Pat. No. 5,276,977 which is assigned to the Assignee of this invention.

STATEMENT OF THE PRESENT INVENTION

Integrating a microalgae production plant with a motor-generator provides a unique synergism. The motor-generator provides electrical energy which is sold for profit and/or used in the microalgae production plant to provide power for circulating the water in the culture pond and for pumping fluids, e.g., an aqueous suspension of microalgae. Artificial illumination also can be provided from the electrical energy. The hot exhaust gases from the generator provide sensible heat for drying the product algae. The drying may be direct or indirect. Carbon dioxide can be recovered from the generator exhaust gases and delivered to the culture pond.

Accordingly the principal object of this invention is to integrate a microalgae production plant with a motor-generator plant.

DESCRIPTION OF THE PREFERRED EMBODIMENTS

Figure 1:
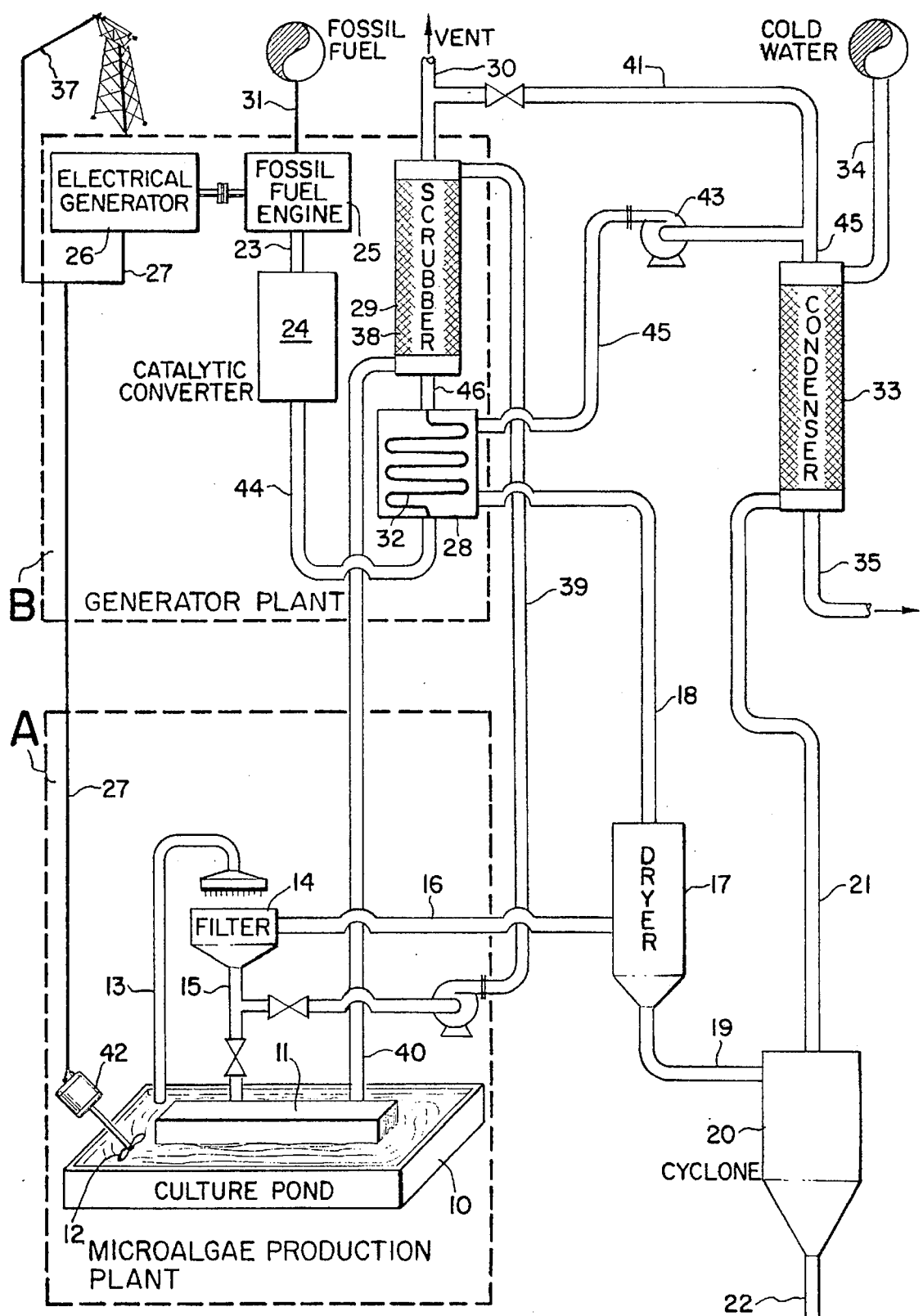
FIG. 1 is a schematic illustration of an a microalgae production plant integrated with a motor-generator plant, including indirect heat transfer from hot exhaust gas for product drying.
Figure 2:
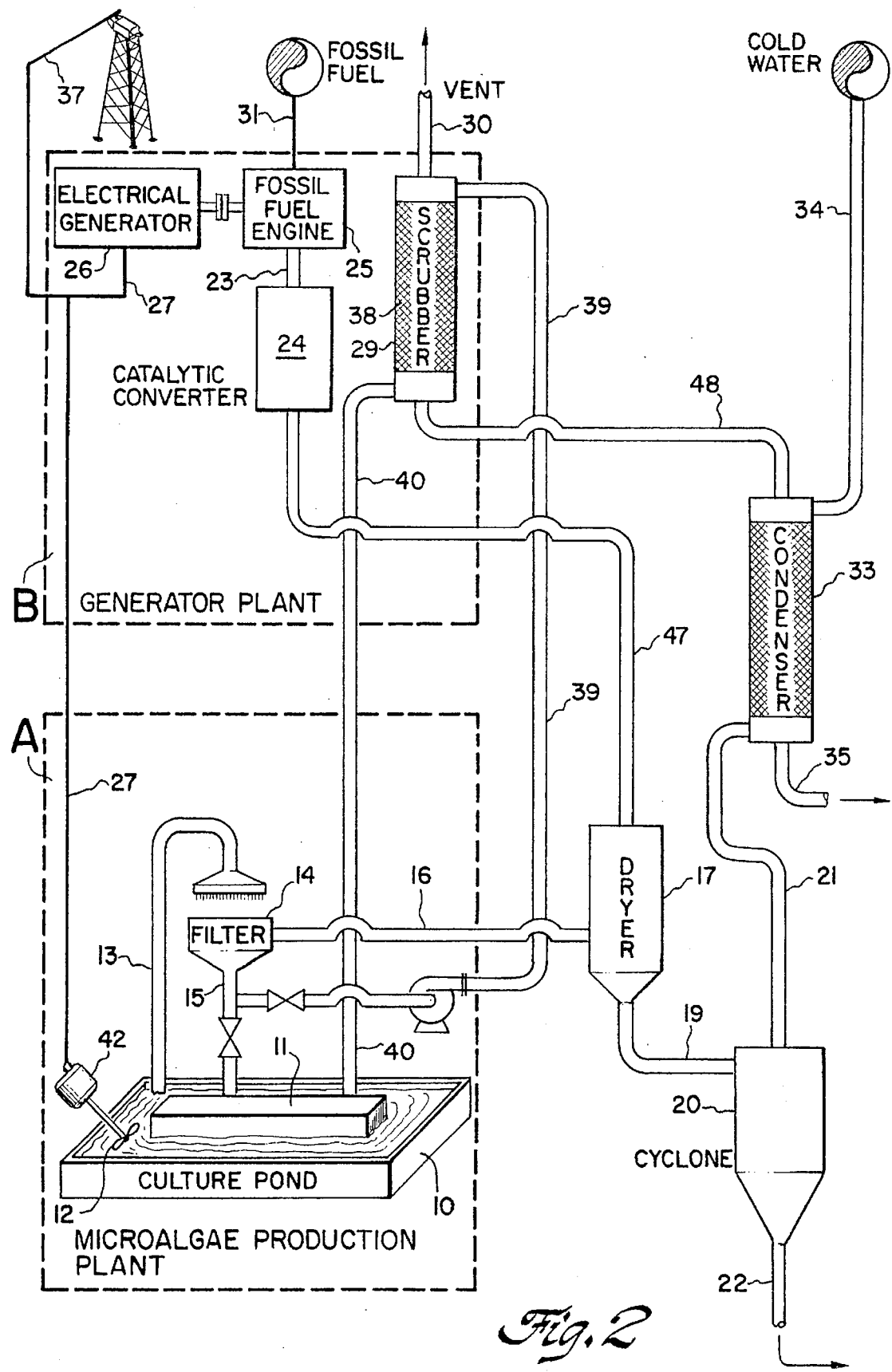
FIG. 2 is a schematic illustration similar to FIG. 1 including direct product heating with hot exhaust gas.

The invention, as illustrated in FIGS. 1 and 2, integrates a microalgae production plant within a bold, broken line A and a motor-generator plant within a bold broken line B. The elements outside the bold broken lines A and B are elements unique to the integration of the two plants.

THE MICROALGAE PRODUCTION PLANT

The invention includes a microalgae culture pond 10, normally an artificial construction from concrete, coated metal or reinforced plastic. A typical culture pond has a surface area of about 0.1 to 2.0 acres and an average depth of about 6 to 15 inches. Smaller culture ponds may not be economical to operate. Larger culture ponds may be difficult to manage. The culture pond requires natural sunlight during daylight hours to promote algae growth. Artificial sunlight in the night may be desirable. The water in the culture pond may be fresh water, brackish water or sea water. A significant concentration of carbon dioxide in the culture pond water promotes algae growth. The water in the culture pond also may be supplemented with minor quantities of selected nutrients, e.g., inorganic salts, vitamins and minerals. Sea water may be used in the culture pond for growing those algae which benefit from sea water.

Selected microalgae are introduced into the culture pond in accordance with the desired product. Preferred microalgae are those which can be harvested, dried and packaged as food products or food supplements. Other microalgae may be selected for use as a source of chemicals, medical extracts, cosmetic extracts or food. Some circulation of the water in the culture pond is preferable. Appropriate circulation can be achieved by having a central dam 11 and a motor-driven impeller 12. A portion of the culture pond inventory is withdrawn continuously or discontinuously through a conduit 13 and delivered to a filter 14. The withdrawn inventory is an aqueous suspension of the microalgae. The aqueous filtrate from filter 14 may be returned to the production pond through a conduit 15. Some or all of the aqueous filtrate may be directed through a conduit 39 as liquid feed to a scrubber 29 and then returned to the culture pond through a conduit 40. The filtrate contains water with dissolved $CO_2$ and residual nutrients. Continuous filters are preferred, e.g., leaf filter, drum filter, vacuum belt filter. Alternately the separation of aqueous materials may occur in vibrating screens, centrifuges, dissolved air flotation, et cetera. The filter cake is recovered from the filter 14 through a conduit 16 and delivered to a spray dryer 17 which receives hot gases from a conduit 18. The hot drying gases may be air, but preferably are inert gas or non-oxidizing gas, e.g., nitrogen, carbon dioxide. The hot drying gases may be the exhaust gas from fossil fuel combustion in a generator, as will be described in connection with FIG. 2. The dried microalgae is delivered as a gaseous stream of particulate microalgae through a conduit 19 to a separation cyclone 20. The hot gases are withdrawn from the cyclone 20 through a conduit 21. The dried microalgae is recovered as a particulate substance through a product conduit 22. All of the equipment and processing described heretofore is available in the prior art. The drying should be carried out at a suitable temperature to avoid heat degradation of the microalgae product.

THE ELECTRICAL GENERATING SYSTEM

The motor-generator plant is conventional and includes a fossil-fuel engine 25, preferably a diesel engine, which drives an electrical generator 26 generating electrical power which is delivered through conductors 27. Hot exhaust gases from the fossil-fuel engine 25 are delivered through a manifold conduit 23, a catalytic converter 24, a heat exchanger 28, a $CO_2$ scrubber 29 and then vented to the atmosphere through a conduit 30. Diesel oil, or other hydrocarbonaceous fuel, is delivered through a conduit 31 to the fossil-fuel engine 25. Gasoline, kerosene or propane engines are preferred as the fossil-fuel engine 25.

The catalytic converter 24 is provided to eliminate objectionable organic compounds (e.g., aldehydes) from the hot fossil-fuel exhaust gases. In the heat exchanger 28, the hot fossil-fuel exhaust gas passes through heating coils 32 which release thermal energy to a circulating stream of inert dryer gases passing from the conduit 45 to conduit 18, the spray dryer 17, the conduit 19, the separation cyclone 20, the conduit 21 and a condenser 33.

Cold water enters the condenser 33 from a conduit 34. Cold water and condensed water vapor from the conduit 21 are collected in the condenser 33 and delivered through a conduit 35 as condensate. Condensate in the conduit 35 may contain small amounts of dried algae which pass through the separation cyclone 20. By cooling the circulating gas stream in the condenser 33, a gas stream of low water content is recovered from the top of the condenser 33 through a conduit 45. The cooled, low-water-content gas stream is fed to the heat exchanger 28, heated therein by heat exchange with the hot coils 32, and recovered as a hot, relatively dry gas in the conduit 18. A pump 43 may be provided to advance the gas in conduit 45.

Cooled fossil-fuel exhaust gas from the hot coils 32 is delivered from the heat exchanger 28 through a conduit 46 to the base of the $CO_2$ scrubber 29. The $CO_2$ scrubber 29 may be a column having appropriate liquid-gas contact packing 38. Aqueous filtrate is delivered to the top of the scrubber 29 through a conduit 39. The aqueous filtrate within the scrubber 29 absorbs carbon dioxide from the cooled exhaust gas from conduit 46 and delivers an aqueous stream containing dissolved carbon dioxide through a conduit 40 to the culture pond 10 as a make-up water supply and make-up $CO_2$ supply. The cooled exhaust gases from the scrubber 29 are vented to the atmosphere through a conduit 30. A portion of the vent gas may be diverted through a conduit 41 to the recirculating inert gas stream in conduit 45 as replacement gas.

In the alternative embodiment of FIG. 2, the heat exchanger 28 and heat transfer coils 32 are eliminated. Hot exhaust gas from a conduit 47 is employed directly as the drying gas in the dryer 17. The hot gases entrain dried algae and move through conduit 19 to the cyclone separator 20. The hot gas passes through the conduit 21 to the condenser 33. The hot gas is cooled and residual entrained algae are removed in a conduit 35. Cooled exhaust gas is delivered through conduit 47 to the $CO_2$ scrubber 29 and vented to the atmosphere through conduit 30.

The cooling water may be fresh water or sea water. A preferred source of cooling water is sea water obtained from a depth of at least 1,000 feet as described in U.S. Pat. No. 5,276,977 at temperatures below 60° F.

ELECTRICAL INTEGRATION

The electrical power generator 26 preferably is sized to supply all of the electricity requirements of the integrated plant. Preferably a major portion of the available electrical power is delivered to the microalgae production plant for energy needs, e.g., the motor 42 which drives the impeller 12 to provide movement of the water in the culture pond 10. Some electrical power may provide illumination for the plant and artificial sunlight for the culture pond 10 when and if required. Other electrical power may drive pumps for moving gases, water and water suspensions through the microalgae production plant and to supply power for meters and automatic controls.

Excess electrical power from the generator 26 may be delivered as a product for sale through electrical conductors 37.

CARBON DIOXIDE

Carbon dioxide is required for appropriate growth of algae. Carbon dioxide is usually available in metal cylinders at substantial expense. For the integrated plant of this invention, carbon dioxide is readily available dissolved in water for immediate use in the production pond.

Carbon dioxide is recovered from the exhaust gases in a $CO_2$ scrubber 29 and delivered, dissolved in water, through a conduit 40 to the culture pond 10. The exhaust gas heat is supplied to dry the microalgae filter cake in a spray dryer 17 to produce a dried particulate algae product through conduit 19 and subsequently through conduit 22.

THERMAL ENERGY

The sensible heat from the hot exhaust gas is transferred in the heat exchanger 28 (FIG. 1) to recirculating inert gas which is the hot gas for the spray dryer 17.

In the embodiment of FIG. 1, a recirculating stream of inert gas passes through the dryer 17, the cyclone separator 20, the condenser 33 and the heat exchanger 28. Appropriate pumps 43 may be employed to recirculate the inert gas. The recirculating stream of inert gas is alternately heated and cooled.

In the embodiment of FIG. 2, no recirculating gas stream is employed. The hot exhaust gas directly provides the thermal energy for drying the microalgae. The exhaust gas passes sequentially through the dryer 17, the cyclone separator 20, the condenser 33 and the $CO_2$ absorber 29 prior to discharge. The exhaust gas thereby supplies heat for product drying and supplies $CO_2$ for feeding the culture pond.

GENERAL

A preferred microalgae is spirulina which is in demand as a food product, usually compacted from the dry powder into pellets for packaging, shipping, storage and consumption. Spirulina is grown in fresh water with appropriate nutrient supplements. Other microalgae use for commercial products are:

chlorella
scenedesmus
synechococcus
anabaena
dunaliella

Optimum operating temperature in the culture pond is from 80° F. to 100° F. Some microalgae thrive at temperatures above or below the stated optimum range for preferred microalgae. Heating or cooling may be applied for culture ponds as desired. Cooling by delivering deep sea water is preferred as a direct or indirect cooling medium. The temperature of the product from the spray dryer 17 preferably is about 180° F.

The moist microalgae delivered to the spray dryer 17 contain about 90 weight percent water. The microalgae product contain about 5 weight percent water.

SUMMARY

The integrated microalgae production/motor-generator presents a source of carbon dioxide for the microalgae production plant; presents electrical energy as required by the microalgae plant; provides electrical energy for motors 42 and pumps 43. The savings to the microalgae production plant offset the expense of capitalizing and operating the motor-generator. No costly external carbon dioxide is required; no costly external electrical energy is required; no costly external thermal energy is required for drying microalgae.

We claim:

1. An integrated plant including a motor-generator plant with a microalgae production plant for growing, drying and harvesting algae, comprising:

A motor-generator fueled with fossil fuel for generating electrical energy and hot exhaust gas containing carbon dioxide;

A microalgae culture pond containing water having a high $CO_2$ content and impeller means for circulating said water;

Collecting means for recovering microalgae and water from said culture pond; dewatering means for recovering moist microalgae; thermal dryer means for drying said moist microalgae to produce dried microalgae as a product;

Means for recovering hot exhaust gas from said motor; means for transferring sensible heat from said hot exhaust gas to dry said moist microalgae;

$CO_2$ recovery means for collecting $CO_2$ from cooled exhaust gas in an aqueous solution; water delivery means for delivering said aqueous solution containing $CO_2$ to said culture pond.

2. The integrated microalgae production/motor-generator plant of claim 1 wherein means are provided to deliver a portion of said electrical energy to drive said impeller means.

3. The integrated microalgae production/motor-generator plant of claim 1 wherein an aqueous stream from a separation means is returned to said culture pond along with said aqueous solution containing $CO_2$ recovered from said exhaust gas.

4. An integrated microalgae production/motor-generator plant of claim 1 wherein:

Said hot exhaust gas is introduced directly into said thermal dryer means to dry a filter cake.

5. An integrated microalgae production/motor-generator plant of claim 1 wherein:

A means for recovering hot exhaust gas from said motor includes heat exchange means for recovering sensible heat from said hot exhaust gas and means for transferring sensible heat to a recirculating inert gas stream; passing said recirculating inert gas through said dryer means to dry said moist microalgae; and means for delivering the cooled exhaust gas to said $CO_2$ recovery means.

6. The integrated microalgae production/motor-generator plant of claim 5 wherein said recirculating inert gas stream passes sequentially through a spray dryer, a separation cyclone, a condenser and said heat exchanger means.

* * * * *